United States Patent
Korver, II et al.

(10) Patent No.: US 6,484,332 B2
(45) Date of Patent: Nov. 26, 2002

(54) SYSTEM FOR VERTICAL TO HORIZONTAL MOVEMENT AND LATERAL MOVEMENT OF A PATIENT

(75) Inventors: Clayton P. Korver, II, Orange City, IA (US); Dana M. Dawson, Cooperstown, NY (US); John G. Schmitz, LeMars, IA (US); Charles B. Reinert, Alton, IA (US)

(73) Assignee: Med-Tec Iowa, Inc., Orange City, IA (US)

( * ) Notice: Subject to any disclaimer, the term of this patent is extended or adjusted under 35 U.S.C. 154(b) by 12 days.

(21) Appl. No.: 09/733,315

(22) Filed: Dec. 8, 2000

(65) Prior Publication Data

US 2002/0095722 A1 Jul. 25, 2002

Related U.S. Application Data (60) Provisional application No. 60/169,583, filed on Dec. 8, 1999.

(51) Int. Cl.$^7$ .................................................. A61G 7/14
(52) U.S. Cl. ..................... 5/81.1 R; 5/81.1 HS; 5/86.1; 5/610; 5/601; 5/624
(58) Field of Search ........................... 5/601, 610, 624, 5/81.1 R, 86.1, 81.1 HS; 378/209

(56) References Cited

U.S. PATENT DOCUMENTS

| | | |
|---|---|---|
| 1,631,888 A | 6/1927 | Pow |
| 2,295,006 A * | 9/1942 | Philips .................... 280/242.1 |
| 2,787,506 A | 4/1957 | Travisano .................... 311/10 |
| 3,069,543 A | 12/1962 | Sazavsky ..................... 250/55 |
| 3,262,133 A * | 7/1966 | Beitzel .......................... 5/429 |
| 3,640,520 A | 2/1972 | Wieland et al. ............. 269/323 |
| 3,786,523 A | 1/1974 | Sele ............................ 5/81 B |
| 3,806,109 A * | 4/1974 | Weber et al. ................ 378/209 |
| 3,997,926 A * | 12/1976 | England ......................... 5/610 |
| D249,359 S | 9/1978 | Stott et al. ..................... D24/6 |
| 4,125,907 A | 11/1978 | Junginger et al. ............. 5/81 B |
| 4,259,756 A * | 4/1981 | Pace ............................. 5/425 |
| 4,603,845 A | 8/1986 | Schmedemann ............ 269/323 |
| 4,841,585 A | 6/1989 | Masuzawa ....................... 5/62 |
| 5,022,810 A | 6/1991 | Sherrow et al. ............. 414/501 |
| 5,561,873 A | 10/1996 | Weedling ........................ 5/711 |
| 5,642,537 A | 7/1997 | Johnson ........................ 5/81.1 |
| 5,655,238 A * | 8/1997 | Stickley et al. ................ 5/618 |
| 5,737,781 A | 4/1998 | Votel ............................. 5/81.1 |
| 5,775,337 A | 7/1998 | Hauger et al. .............. 128/869 |
| 5,790,996 A | 8/1998 | Narfstrom ...................... 5/610 |
| 5,806,116 A | 9/1998 | Oliver et al. ................... 5/621 |
| 5,822,814 A | 10/1998 | Van Der Ende ............... 5/601 |
| 5,832,550 A | 11/1998 | Hauger et al. ................. 5/621 |
| 5,848,449 A | 12/1998 | Hauger et al. ................. 5/637 |
| 5,983,424 A * | 11/1999 | Naslund ......................... 5/601 |
| 5,983,426 A | 11/1999 | Vanek et al. ................... 5/621 |
| 6,161,237 A * | 12/2000 | Tang et al. .................. 378/209 |

FOREIGN PATENT DOCUMENTS

| | | | | |
|---|---|---|---|---|
| FR | 1194955 A | * | 11/1959 | ............. 5/81.1 HS |
| GB | 321073 | * | 10/1929 | ............. 5/81.1 HS |

* cited by examiner

*Primary Examiner*—Michael F. Trettel
(74) *Attorney, Agent, or Firm*—McKee, Voorhees & Sease, P.L.C.

(57) ABSTRACT

A patient transfer system is provided for quick, easy and comfortable movement of a patient between horizontal and vertical positions and between lateral locations for medical procedures. The system includes a gurney with a patient positioning board pivotally mounted thereon for movement between horizontal and upright positions. The board is adapted to receive a patient mold. A footrest is provided at the lower end of the board such that a patient can step onto the footrest when the board is in the upright position and lean against the board. The board is then lowered to a horizontal position on the gurney. The gurney can be wheeled into position adjacent a treatment table in a treatment room, such as for radiation therapy, and docked to the table. Laterally extending guide rails on the gurney and on the treatment table are aligned such that the board can be laterally moved from the gurney guide rails to the table guide rails, thereby quickly and easily transferring the patient from the gurney to the treatment table in an indexed known position, which can be duplicated in future treatment procedures.

29 Claims, 6 Drawing Sheets

Fig. 9

SYSTEM FOR VERTICAL TO HORIZONTAL MOVEMENT AND LATERAL MOVEMENT OF A PATIENT

This application claims priority to the previously filed provisional application on Dec. 8, 1999, U.S. Ser. No. 60/169,583.

BACKGROUND OF THE INVENTION

1. Field of the Invention

The present invention relates generally to a patient transfer system and in particular to a patient transfer system wherein an assembly allows for the comfortable transitioning of a patient from a vertical to a horizontal position and wherein a transfer board allows for the transferring of a patient laterally to move to and from a treatment table for a medical procedure.

2. Problems in the Art

Currently, patient transfer systems, such as gurneys, require the patient to transition themselves from a vertical standing position to a horizontal position on the gurney. Such movement may be difficult for elderly, disabled or injured patients.

Many current treatments, such as pelvic area treatments in radiation oncology and certain imaging procedures, require the patient to be placed into a custom mold or vacuum cushion system for accurate repositioning. Many such cushion systems and molds are custom designed for the individual patient. Damage to such molds and cushion systems can and does easily result from the patient's transitioning from the vertical stand-up position to a horizontal position within the mold located on top of the transfer system. It is therefore desirable to have a patient transfer system in which the patient may easily enter the mold so as not to damage the mold. It is further desirable to have a patient transfer system in which the patient is kept as comfortable as possible. There is therefore a need for a patient transfer system in which the patient may enter the mold or cushion system from the vertical position.

Further, transfer of patients from one treatment area to another is often a burdensome, time consuming, and patient discomforting process. Currently, a patient is typically transferred from one area's table to another table using boards which must be slipped under and removed from the a patient prior to treatment. The board and patient are manually moved by two or more people. Such additional movement of the patient adds to the patient's discomfort. Further, the necessity of transferring a patient from a board to the treatment table typically requires numerous care providers, all of whom must give up time which could be spent treating other patients. There is therefore a need to provide a system capable of quickly and easily transferring a patient from a gurney or table to another table for a medical procedure or treatment.

Many current treatments require a patient to be immobilized during treatment. Patients must be in a known or fixed location relative to the treatment table in order to accurately and repeatedly carry out the treatment. Often this requires the patient to be fitted with various positioning devices which can hold a patient still during treatment and/or act as a reference for the care provider to use during treatment. Many such devices are customized for the treatment and for the patient. There is therefore a need for a patient transfer system which is capable of keeping a patient immobile or in a fixed, known position relative to the treatment table. This patient transfer system must accommodate any customized immobilization device on a per patient basis.

Further, current systems use various points throughout the treatment room for reference or indexing during treatment. Many treatment and imaging devices are located at a fixed position relative to the room coordinates and therefore require the patient to be placed in a specific spot within the room. Therefore there is a need for a patient transfer device that places the patient repeatedly in the exact position on the patient support assembly and that incorporates any markers or localizing accessory to easily position the patient relative to the room coordinates. Further, current imaging, surgical and therapy procedures all take place in dedicated areas within the hospital that are costly to maintain. There is therefore a need for a patient transfer system that allows the care provider to fully prepare the patient in another area within the facility and when the therapy, imaging or surgical area is available, transfer the patient on to the specific patient support assembly.

There is therefore a need for a patient transfer system which avoids these and other problems.

Features Of The Invention

A general feature of the present invention is the provision of patient transfer system which overcomes the problems found in the prior art.

A further feature of the present invention is the provision of a patient transfer system which can quickly and easily transfer any patient from the vertical to the horizontal position.

A further feature of the present invention is the provision of a patient transfer system which allows a patient to enter a mold or cushion system from the vertical position, without damaging the mold or cushion.

Another feature of the present invention is the provision of a patient transfer system which allows for the quick and easy transfer of a patient to and from a medical treatment table or procedure area.

A further feature is the provision of a patient transfer system which allows staging of multiple patients so as to increase throughput for medical procedures.

A still further feature of the present invention is the provision of a patient transfer system which provides for attachment of patient based reference markers and localizers for positioning the patient relative to the room coordinates.

Another feature of the present invention is the provision of a patient transfer system which is easily movable.

These, as well as other features and advantages of the present invention, will become apparent from the following specification and claims.

SUMMARY OF THE INVENTION

The present invention generally comprises a patient treatment system in which there is a pivotal patient positioning board mounted on a gurney for rotation between vertical and horizontal positions. The board can also be laterally moved from the gurney to a treatment table or imaging table to quickly and easily move the patient to and from the table for performing the medical procedure. The board slides, rolls or otherwise moves from the gurney to the treatment table.

The table normally includes a mold and indexing means to allow accurate repeatable positioning of the patient for medical procedures, such as imagining, simulation, radiation therapy and/or surgery. The transfer board will accommodate the attachment of localizer frames, markers, patient monitoring devices, mechanical interstitial devices, ultrasound devices and immobilization devices. The invention also is provided to accommodate different height patients.

DETAILED DESCRIPTION OF THE INVENTION

The present invention will be described as it applies to its preferred embodiment. It is not intended that the present invention be limited to the described embodiment. It is intended that the invention cover all modifications and alternatives which may be included within the spirit and scope of the invention.

The patient transfer system of the present invention is generally designated by the reference numeral 10 in the drawings. The system 10 generally comprises a gurney 12, a treatment table or couch 14, and a patient positioning board 16 which is moveable between the gurney 12 and the table 14. The gurney 12 includes wheels 18 so that the gurney may be rolled along a floor toward and away from the table 14.

Figure 1:
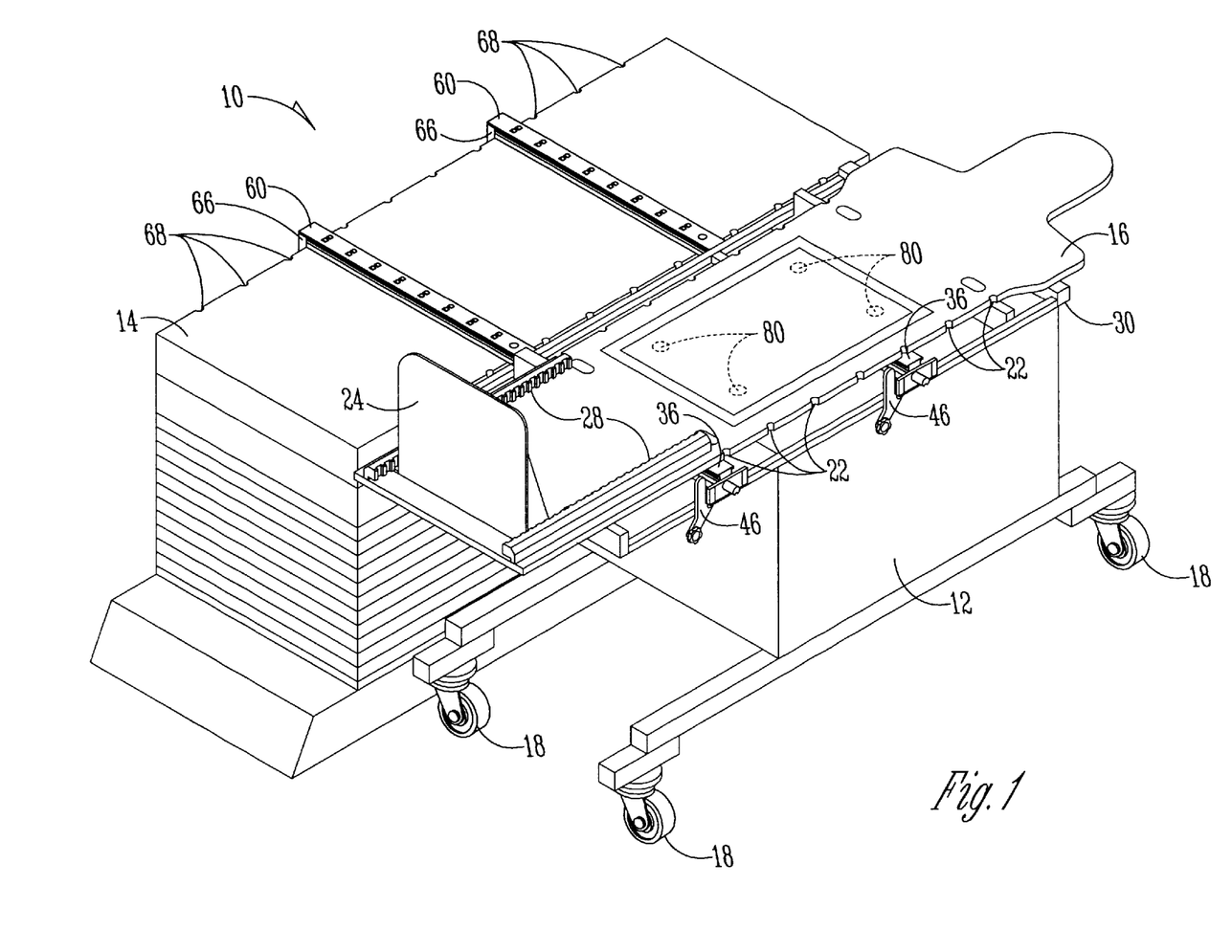
FIG. 1 is a perspective view of the system, with the patient positioning board positioned on a gurney in a horizontal orientation.
Figure 2:
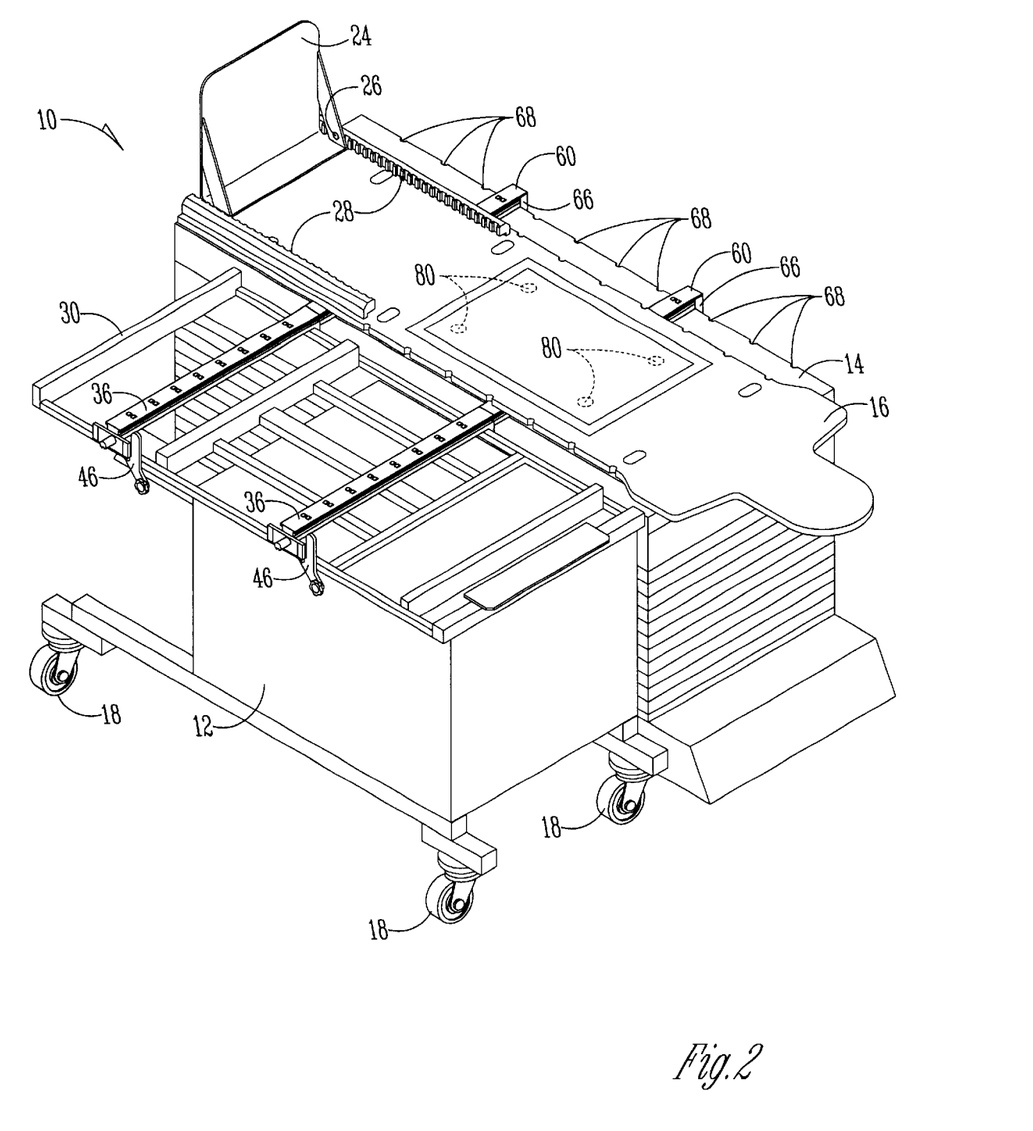
FIG. 2 is another perspective view of the system, with the patient positioning board positioned on the treatment table.
Figure 3:
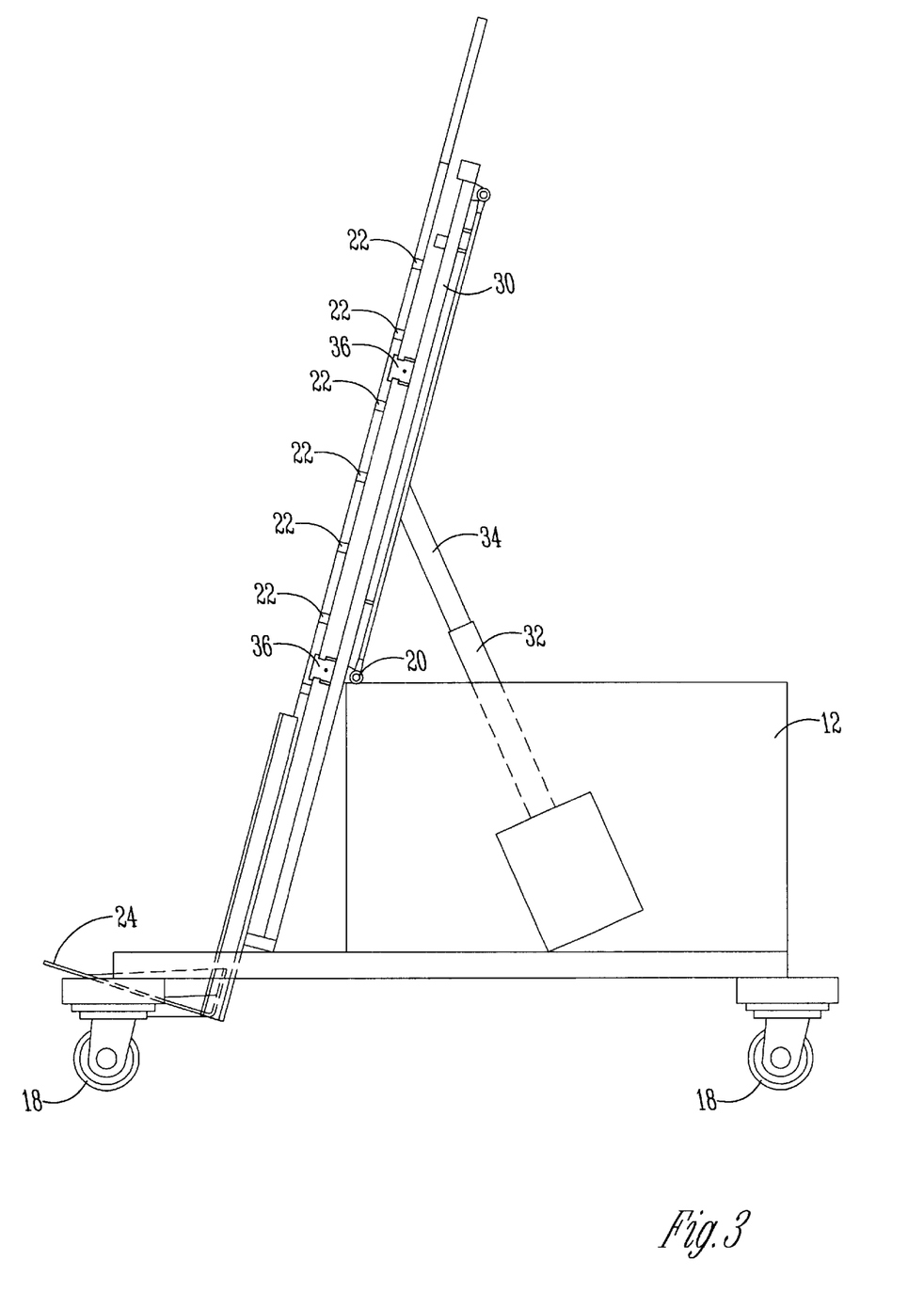
FIG. 3 is a perspective view of the gurney showing the patient positioning board moved to its upright position.
Figure 4:
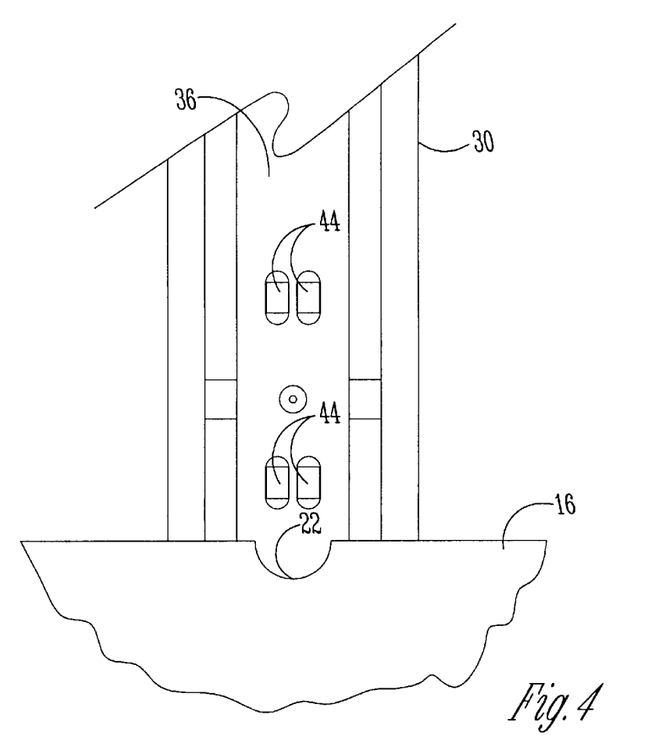
FIG. 4 is a partial top plan view showing one of the guide rails on the gurney.

The board 16 is pivotally mounted on the gurney 12 via a horizontal axle 20 for rotation between a horizontal position shown in FIG. 1 and an upright position shown in FIG. 3. The board 16 has opposite sides each having a plurality of notches 22. A footrest 24 is adjustably mounted on the lower end of the board 16 and includes a retractable detent 26 on each side for selective receipt in one of a plurality of teeth 28 on the opposite sides of the board 16 at the lower end thereof. The detents 26 may be spring loaded so as to be normally biased outwardly into engagement with one of the teeth 28, with a knob or tab to pull so as to release the detents 26 from the teeth such that the foot rest 24 can be raised or lowered. The adjustability of the footrest 18 accommodates different patient heights, and insures that the torso of the patient is always located in the same position on the board 16.

The gurney 12 includes an upper frame 30 to which the board 16 is mounted. A linear actuator such as a hydraulic cylinder or other telescoping arm assembly 32 is mounted in the gurney with the extensible arm 34 attached to the frame 30 of the gurney 12. Upon extension of the arm 34, the frame 30 and board 16 are raised from the horizontal position shown in FIG. 1 to the upright position shown in FIG. 3. In the upright position, a patient can easily step onto the footrest 24 and lean against the board 16. The patient can be strapped to the board using any convenient means. The arm 34 can then be retracted so as to lower the frame 30 and board 16 to the horizontal position shown in FIG. 1. Thus, the patient can be quickly and easily moved from a standing position to a laying position on the board 16.

As an alternative to the hydraulic cylinder 32, any other convenient means can be used to move the frame 30 and board 16 between the horizontal and upright positions. Counterweights may also be used so as to counter-balance the weight of the patient the pivotal board 12.

Figure 5:
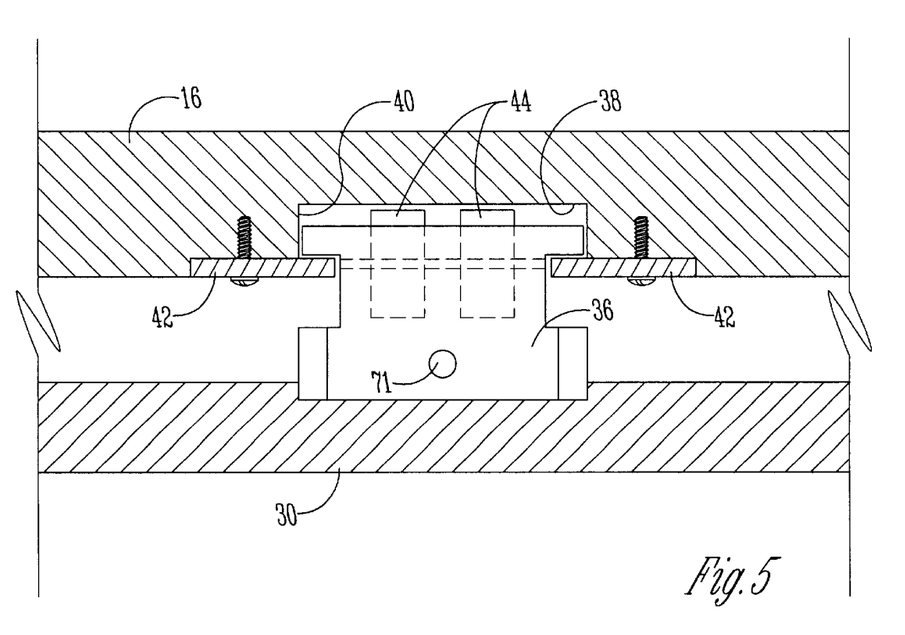
FIG. 5 is a sectional view taken along lines 5—5 of FIG. 1.

The board 16 is also laterally moveable relative to the gurney frame 30. More particularly, the frame 30 includes at least two guide rails 36 extending laterally across the top of the gurney 12. The guide rails 36 are received within guide tracks 38 on the bottom of the board 16. In a preferred embodiment, the guide rails 36 are T-shaped in cross section, with the guide tracks 38 having a mating T-shape, as best seen in FIG. 5. The T-shape of each guide track 38 is formed by a slot 40 in the bottom of the board 16 and a pair of friction bars or retainer strips 42 mounted to the bottom of the board with inner edges extending toward one another beyond the side edges of the slot 40. Preferably, the guide rails 36 each include a plurality of rollers 44, upon which the board 16 rolls. Alternatively, the rollers may be provided in the slot 40 of the board for rolling along the top surface of the guide rails 36. As a further alternative, the guide rails 36 and guide tracks 38 can be made of low friction material, with lubrication to allow the board 16 to slide along the rails 36.

Figure 6:
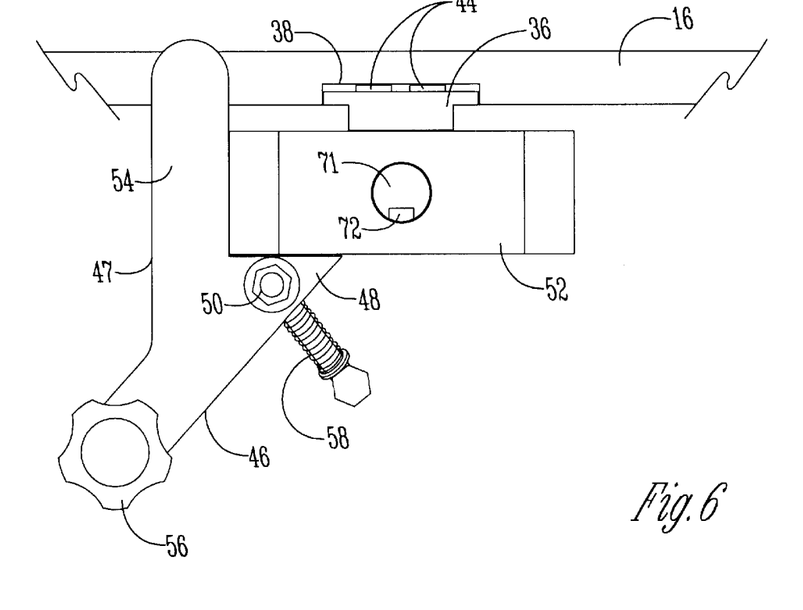
FIG. 6 is a side elevation view showing the lock mechanism in a locked position to preclude lateral movement of the board relative to the gurney.
Figure 7:
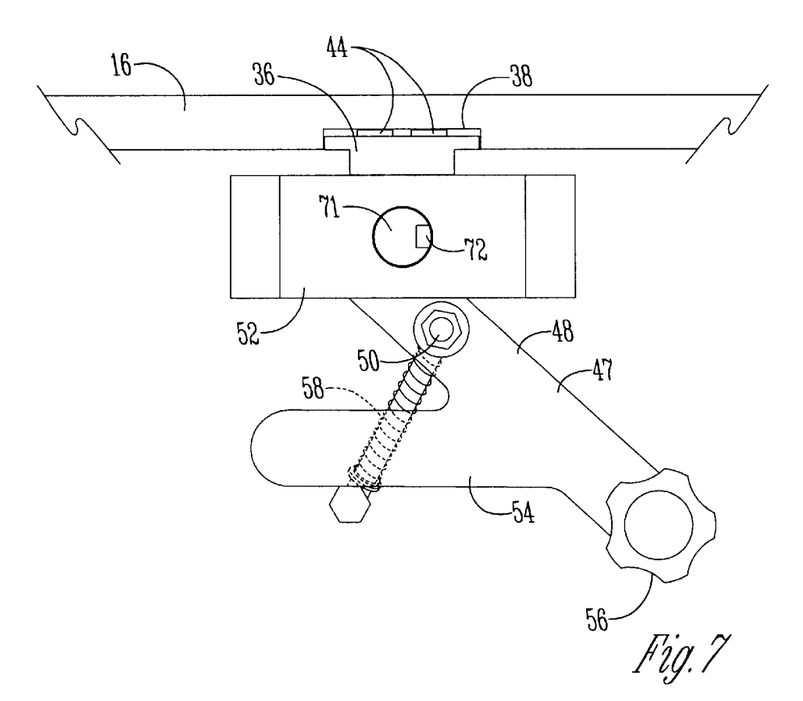
FIG. 7 is a view similar to FIG. 6 showing the lock mechanism in an unlocked position.

Each end of each guide rail 36 includes a lock mechanism 46, best seen in FIGS. 6 and 7. The lock mechanism 46 includes a Y-shaped member 47 having a right branch 48 secured to a pivot axis 50 on the gurney frame 30. The left branch 54 of the lock mechanism 46 extends upwardly in the lock position to block lateral movement of the board 16 relative to the gurney 12, as shown in FIG. 6. The lower end or base of the Y-shaped member 47 includes a knob 56 to form a handle so that the Y-shaped member 47 can be moved to an unlocked or release position, as shown in FIG. 7. By moving the handle 56 approximately 90° in a counterclockwise direction, such that the left branch 54 is moved from the locked to unlocked position away from the board 16, the board can be moved along the guide rails 36. The lock mechanism 46 also includes a spring loaded rod 58 having a lower end connected to the gurney 12 and an upper end connected to the Y-shaped member 47 so as to urge the Y-shaped member to the locked or unlocked position. The lock mechanisms 46 may be interconnected by rods or bars such that movement of one handle 56 automatically moves the other handles 56 in unison between the locked and unlocked positions.

Figure 8:
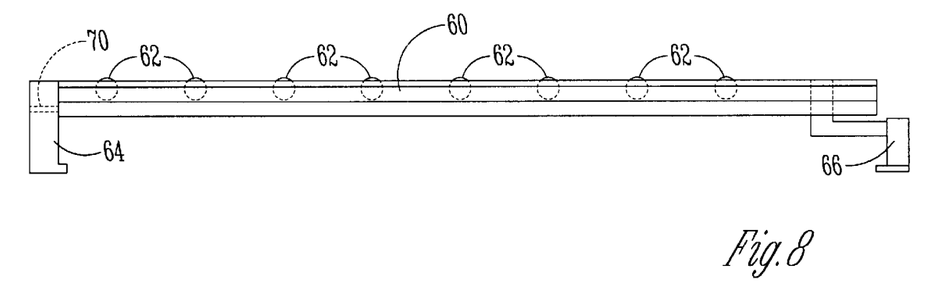
FIG. 8 is a side elevation view showing one of the guide rails for the treatment table.

A second set of guide rails 60 similar to guide rails 36 are adapted to be installed on the treatment table 14. The treatment table guide rails 60 are shown in FIG. 8 and generally include a T-shaped cross-section for receipt of the guide rails 60 into the guide tracks 38 of the board 16. Preferably, the guide rails 60 include a plurality of rollers 62 similar to those described above with respect to guide rails 36. One end of each guide rail 60 includes a block 64 adapted to overlappingly engage one side edge of the treatment table 14. The opposite end of the guide rail 60 includes a pivotal eccentric cam 66 which is adapted to lockingly engage one of a plurality of notches 68 extending along the opposite sides of the treatment table 14. The structure and operation of the eccentric cam 66 is described in U.S. Pat. No. 5,806,116, which is incorporated herein by reference.

The guide rails 60 are positioned on the treatment table 14 so as to be aligned with the guide rails 36 on the gurney 12 when the gurney is positioned adjacent the table 14 for transferring a patient from the gurney 12 to the table. The end blocks 64 of the guide rails 60 are on the side of the table 14 adjacent to the gurney 12. The end blocks 64 include a laterally extending hole 70 which is adapted to receive the end of a shaft 71 extending outwardly from the adjacent end of the guide rails 36, so as to maintain the alignment of the gurney 12 with the table 14. Preferably, the end of the shaft 71 includes a key slot 72 adapted to receive a key pin (not shown) in the hole 70. Upon movement of the lock mechanism 46 from the locked to the unlocked position, the Y-shaped member 47 rotates the shaft 71 approximately 90 degrees to lock the key pin (not shown) in the key slot 72, thereby locking the gurney 12 to the table 14. Other convenient methods of interlocking or docking the gurney to the table may also be utilized, such as clamps, or overlapping structure, or electro-mechanical latches.

Figure 9:
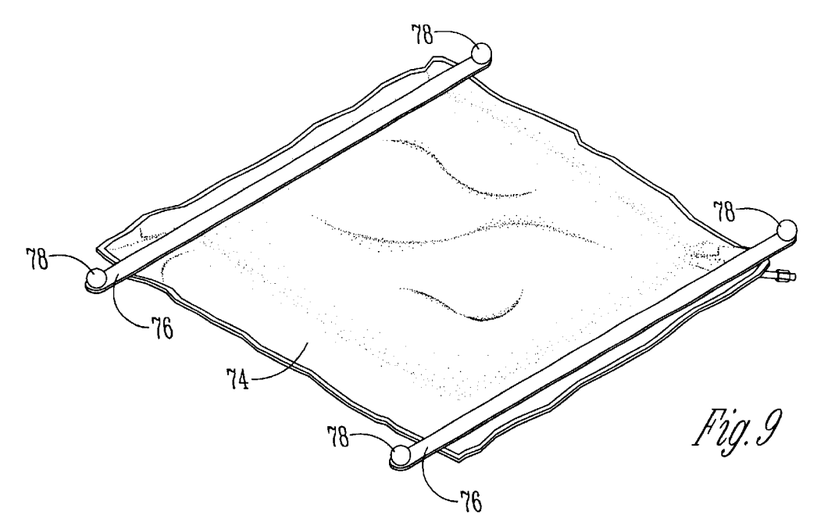
FIG. 9 is a perspective view of the bottom side of a patient positioning mold used on the patient positioning board of the present invention.

The board 16 is also adapted to receive a patient positioning cushion or mold 74, such as that disclosed in U.S. Pat. No. 5,832,588, which is incorporated herein by reference. The mold 74 is generally shown in FIG. 9 and includes indexing securement bars 76. Preferably, the opposite ends of the securement bars 76 include a snap ball 78 for snap fitting into one of the notches 22 on the board 16. This type of snap fit interlock system is described in Applicant's U.S. Pat. No. 6,161,237 (to be issued Dec. 19, 2000) and entitled "Patient Positioning Device For Radiation Therapy," which is incorporated herein by reference. As an alternative to the snap fit balls 78, the ends of the mold securement bars 76 may include eccentric cams, similar to cam 66 described above, for securing the mold 74 to the board 16 via the indexing notches 22.

The board 16 is preferably made out of a radio translucent material, such as carbon fiber, so as not to be seen during various imaging procedures. The surface of the board is thus an image-friendly material which allows for various imaging modalities. The board 16 may also include embedded fiduciaries or markers 80 to provide geometric references for the location of the board 16 within the treatment room.

In use, the board 16 is moved to the upright position by actuating the hydraulic cylinder 32 or other tilting mechanism. The footrest 24 is adjusted to the desired height, depending upon the patient's height for the proper positioning of the patient on the board 16. Preferably, the mold 74 is secured to the board 16 by snapping the balls 78 into the appropriate notches 22 on the board 16. The patient can then easily step onto the footrest 24 and lean against the board 16. If desired, the patient can be strapped to the board 16 using conventional strapping systems. The hydraulic cylinder 32 or tilting mechanism is then actuated to lower the board to the horizontal position. Thus, the patient has been quickly and easily transferred from a vertical position to a horizontal position without damaging the mold 74. Also, the patient is in a known indexed position on the board 16 due to the indexing of the mold 74, such that the position can be quickly and easily replicated for subsequent treatment procedures.

The board 16 with the patient thereon can be easily transferred to the treatment table 14. To do so, the gurney 12 is rolled into position adjacent the table 14, such that the guide rails 36 on the gurney 12 align with the guide rails 60 on the table 14. The lock mechanisms, which are normally in the locked position when the patient gets onto the board 16, are moved to the unlocked or release position, which lockingly docks the gurney 12 to the table 14, as described above. The board 16 is then rolled from the guide rails 36 onto the guide rails 60. Since the table 16 is stationary, no lock or stop mechanism is shown on the guide rail 60. However, a lock or stop mechanism may be provided on the guide rail 60, to secure the board 16 against movement relative to the table 14.

The above steps are reversed to transfer the board 16 and patient back to the gurney 12 and then move from the horizontal to the upright position, such that the patient can quickly and easily exit the board 16.

With the patient transfer system of the present invention, the patient may be prepped for various treatments without requiring the patient to be transferred from one treatment table to another. Further, individual treatment areas may be prepped on the patient with the prior knowledge of where the patient will be positioned on the board 16 during the treatment.

The board 16 may also include peg holes to accommodate various treatment devices or modular procedure enhancements. For example, the immobilization device as described in U.S. Pat. No. 5,848,449 and 5,775,337 may be used on the board 16. Attachments, including various treatment and monitoring devices, may be secured via an interlocking system to the board 16 by inserting the attachment frame into the peg holes. By securing a device, such as a camera, digitized arm, or the like, to the board 16, the care provider can use the board 16 with the patient secured thereto as a point of reference for various medical procedures, such as the placing of radioactive seeds, and biopsy procedures. This improves the safety of such procedures while minimizing the space needed to perform such procedures.

It is understood that alternative structures can be provided for the tilting of the board 16 and the lateral movement of the board 16 from the gurney 12 to the table 14. For example, as an alternative to the guide rails with the rollers, low friction slidable material, linear actuators, mechanical screws, or hydraulic cylinders may be used to move the board from the gurney 12 to the treatment or imaging table 14. It is preferred that the lateral movement structure accurately transfer the board 16 to the exact same position on the treatment or imaging table 14 every time, thereby allowing care providers to accurately plan for and set up treatments.

With the patient transfer system of the present invention, the board 16 moves precisely and maintains proper positioning of the patient by precisely locating the patient on the board and precisely moving the board onto the treatment table. Such exact positioning or indexing of the board and patient allows for image fusion, wherein one image is laid over another, since the patient is indexed to an exact position on the treatment table and in the treatment room.

Thus, the patient transfer system 10 of the present invention allows for quick, easy and comfortable movement of the patient between horizontal and vertical positions and between lateral locations for medical procedures. The system 10 also minimizes the time requirements for positioning a patient. Multiple gurneys 12 with boards 16 may be used to prepare multiple patients for sequentially staged medical procedures on the table 14, thereby increasing the through put of patients through such procedures and minimizing down time of expensive medical equipment. The system 10 also indexes and locates each patient relative to the transfer board 16 for precise repeat medical treatments, such as radiation therapy.

A general description of the present invention as well as a preferred embodiment of the present invention has been set forth above. Those skilled in the art to which the present invention pertains will recognize and be able to practice additional variations in the methods and systems described which fall within the teachings of this invention. Accordingly, all such modifications and additions are deemed to be within the scope of the invention which is to be limited only by the claims appended hereto.

What is claimed is:

1. A device for positioning a patient onto a table for radiation therapy or imaging procedures, comprising:
   a gurney having wheels for rolling the gurney upon a floor;
   a frame pivotally secured to the gurney for pivotal movement about a horizontal axis between a horizontal position and an upright position;
   a plurality of guide rails extending laterally across the frame;
   a patient transfer board mounted on the frame for pivotal movement therewith, and having opposite sides and opposite top and bottom surfaces;
   a plurality of guide tracks extending laterally across the bottom surface of the board to matingly receive the guide rails such that the board is laterally movable along the guide rails from a position on the frame to a position on the table; and
   a footrest mounted on the board at one end thereof.

2. The device of claim 1 further comprising a linear actuator mounted in the gurney and having an extensible arm connected to the frame for pivoting the frame and board between the horizontal and upright positions.

3. The device of claim 1 wherein the guide rails each have a plurality of rollers for rollably supporting the board on the frame for rolling movement between the frame and the treatment table.

4. The device of claim 1 further comprising a lock mechanism for locking the board to the frame.

5. The device of claim 1 further comprising a lock mechanism for locking the frame to the treatment table.

6. The device of claim 1 wherein the board includes imbedded markers to provide geometric therapy reference points.

7. The device of claim 1 wherein the footrest is adjustable on the board between raised and lowered positions.

8. The device of claim 1 wherein the board is removed from the frame when positioned on the treatment table such that the gurney and frame can be moved away from the treatment table while the board remains on the table.

9. The device of claim 1 wherein the board is made of radio translucent material.

10. The device of claim 1 wherein the board includes indexing notches along the opposite sides for selectively receiving a patient mold.

11. The device of claim 10 wherein the board is adapted to automatically align on the treatment table for precise positioning of the patient on the table.

12. A patient transfer system for moving a patient from a gurney to a table for a medical procedure, comprising:
   a gurney having a plurality of guide rails;
   a table with a plurality of guide rails; and
   a patient transfer board pivotally mounted to the gurney for pivotal movement about a horizontal axis between horizontal and upright positions, the board having a plurality of guide tracks for matingly engaging the gurney guide rails for movement therealong and for matingly engaging the table guide rails for movement therealong.

13. The system of claim 12 further comprising a first lock mechanism for locking the gurney to the table.

14. The system of claim 12 further comprising a second lock mechanism for locking the board to the gurney and to the table.

15. The system of claim 12 wherein the board includes indexing notches to receive a patient mold.

16. The system of claim 12 wherein the board includes markers to provide geometric reference points.

17. The system of claim 12 wherein the board is radio translucent.

18. The system of claim 12 further comprising a linear actuator mounted in the gurney and having an extensible arm connected to the board for pivoting the board between the horizontal and upright positions.

19. The system of claim 12 further comprising a footrest mounted to one end of the board.

20. A method of transferring a patient from a gurney to a table for a medical procedure, comprising:
   setting a patient transfer board mounted on the gurney to an upright position, the board having a footrest;
   standing the patient on the footrest;
   pivoting the board to a horizontal position so the patient is lying on the board;
   positioning the gurney adjacent the table; and
   moving the board and patient laterally from the gurney to the table, so that the board and patient are removed from the gurney and positioned on the table.

21. The method of claim 20 further comprising locking the gurney to the table before the board and patient are moved.

22. The method of claim 21 wherein the lateral movement is accomplished with rollers beneath the board.

23. The method of claim 21 further comprising indexing the patient on the board and the table for precise positioning for radiation treatment.

24. The method of claim 20 further comprising locking the board to the gurney before the board and patient are pivoted.

25. The method of claim 20 further comprising securing a patient positioning mold to the board before the patient stands on the footrest.

26. The method of claim 20 wherein the lateral movement is accomplished with rollers beneath the board.

27. The method of claim 20 wherein the pivotal movement is accomplished with a linear actuator extending between the gurney and the board.

28. The method of claim 20 further comprising indexing the patient on the board and the table for precise positioning for radiation treatment.

29. A method of transferring a patient from a gurney to a table for a medical procedure, comprising:
   moving a patient from a vertical position to a horizontal position on a transfer board on a gurney;
   positioning the gurney adjacent the table; locking the gurney to the table; and then
   moving the board and patient laterally from the gurney to the table, so that the board and patient are removed from the gurney and positioned on the table.

* * * * *